(12) United States Patent
Bitterlich et al.

(10) Patent No.: US 6,730,808 B2
(45) Date of Patent: May 4, 2004

(54) OXIDATIVE REACTIONS USING MEMBRANES THAT SELECTIVELY CONDUCT OXYGEN

(75) Inventors: Stefan Bitterlich, Dirmstein (DE); Hartwig Voss, Frankenthal (DE); Hartmut Hibst, Schriesheim (DE); Andreas Tenten, Maikammer (DE); Ingolf Voigt, Jena (DE); Ute Pippardt, Weissenborn (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/130,822

(22) PCT Filed: Dec. 11, 2000

(86) PCT No.: PCT/EP00/12497

§ 371 (c)(1),
(2), (4) Date: May 23, 2002

(87) PCT Pub. No.: WO01/41924

PCT Pub. Date: Jun. 14, 2001

(65) Prior Publication Data

US 2002/0173422 A1 Nov. 21, 2002

(30) Foreign Application Priority Data

Dec. 10, 1999 (DE) .......................... 199 59 873

(51) Int. Cl.$^7$ ...................... C07C 51/16; C07C 331/00; C07D 209/48; C07D 307/89; B01J 20/28

(52) U.S. Cl. ...................... 562/532; 562/538; 562/542; 562/416; 558/308; 548/476; 549/248; 502/4; 502/302; 502/303; 502/304; 502/324; 502/340; 502/341

(58) Field of Search .................. 502/4, 302, 303, 502/304, 324, 340, 341, 525; 562/532, 538, 542, 416; 558/308; 548/476; 549/248

(56) References Cited

U.S. PATENT DOCUMENTS

| | | | | |
|---|---|---|---|---|
| 4,003,845 A | * | 1/1977 | Van Den Boom et al. | 252/301.4 R |
| 4,791,079 A | | 12/1988 | Hazbun | |
| 4,827,071 A | | 5/1989 | Hazbun | |
| 5,019,306 A | * | 5/1991 | Huang et al. | 264/66 |
| 5,346,720 A | * | 9/1994 | Lombard et al. | 427/101 |
| 5,830,822 A | | 11/1998 | Euzen | |
| 5,849,659 A | | 12/1998 | Tanaka | |
| 5,939,354 A | * | 8/1999 | Golden | 502/525 |
| 6,033,632 A | * | 3/2000 | Schwartz et al. | 422/190 |
| 6,146,549 A | * | 11/2000 | Mackay et al. | 252/373 |
| 6,214,757 B1 | * | 4/2001 | Schwartz et al. | 502/4 |
| 6,352,955 B1 | * | 3/2002 | Golden | 502/302 |
| 6,471,921 B1 | * | 10/2002 | Van Calcar et al. | 422/239 |

FOREIGN PATENT DOCUMENTS

| | | |
|---|---|---|
| EP | 399 833 | 11/1990 |
| EP | 641 749 | 3/1995 |
| EP | 663 232 | 7/1995 |
| EP | 963 788 | 12/1999 |
| WO | 98/41394 | 9/1998 |
| WO | 99/21649 | 5/1999 |

\* cited by examiner

*Primary Examiner*—Cam N. Nguyen
(74) *Attorney, Agent, or Firm*—Keil B. Weinkauf

(57) ABSTRACT

Reactor membranes for used in oxidation reactions of hydrocarbons involving oxygen comprising a selective oxidation catalyst on a mixed conducting, oxide ion selective ceramic membrane of the composition $(Sr_{1-x}Ca_x)_{1-y}A_yMn_{1-z}B_zO_{3-\delta}$, where A is Ba, Pb, Na, K, Y, an element of the lanthanide group or a combination thereof, B is Mg, Al, Ga, In, Sn, an element of the 3d or 4d period or a combination thereof, x is from 0.2 to 0.8, y is from 0 to 0.4, z is from 0 to 0.6, and $\delta$ is a number, dependent on x, y and z, that renders the composition charge neutral.

16 Claims, No Drawings

OXIDATIVE REACTIONS USING MEMBRANES THAT SELECTIVELY CONDUCT OXYGEN

TECHNICAL FIELD

The present invention relates to the field of heterogeneous catalysis. More particularly, the present invention relates to oxidation reactions carried out over a heterogeneous catalyst mounted on a mixed conductive membrane. Such membranes possess electron conductivity as well as selective conductivity for oxygen ions.

BACKGROUND ART

Oxygen permeable membranes whereby oxygen may be selectively transported through the membranes are well known. Such membranes make it possible to separate oxygen from oxygen-containing mixtures with other, preferably gaseous, elements. The selectivity is due to the migration of $O^{2-}$ ions through a layer composed of certain ceramic materials. Before the oxygen passes through the membrane, electrons are transferred to the oxygen on one side of the membrane. After migration through the membrane to the other side, the oxide ions recombine to form oxygen molecules while the electrons migrate in the opposite direction. The ceramic materials mentioned are for instance oxidic compounds of transition metals. These have to have crystallographic vacancies in the lattice for oxygen ion transport to take place.

These lattice vacancies can be produced for example by replacing metal ions in a given oxide with ions of some other valency. This creates in a relatively simple manner $O^{2-}$ vacancies via which the oxide ions are transported to the other end of the membrane.

The best-known oxygen selective ceramic material is $ZrO_2$, where oxide ion conductivity is generated by partly replacing the tetravalent zirconium with trivalent yttrium or divalent calcium ions. Using such a material as an oxygen selective membrane provides a material enabling the transport of $O^{2-}$ ions. The material has no electron conductivity. Such a material is accordingly in itself not capable of transporting oxygen. If oxygen is to be transported through a membrane composed of such a material, an external circuit has to be applied to electrodes mounted on both sides of the membrane in order that charge equalization may be ensured.

To eliminate the need to apply external circuitry, it has been proposed to produce membranes that possess electron conductivity as well as oxide ion conductivity. This is generally achieved on adding a second component possessing good electron conductivity to the ceramic membrane. Palladium, platinum, silver or gold or conductive oxidic compounds of these or other metals are frequently used for this purpose. This gives rise to dual phase membranes. These are disclosed for example in EP-A-399 833. EP-A-399 833 describes inter alia electron conducting as well as oxygen selective membranes comprising a mixture of from 25 to 99% by volume of yttrium-doped zirconia and from 1 to 75% by volume of platinum. Such membranes are then used in oxidation reactions in which oxygen is selectively extracted from mixtures by the membrane and fed to the reaction.

A further development of the above-described membranes is mixed conducting membranes. These are made of not two different materials or phases but a single material capable of selectively conducting not only oxide ions but also electrons. These conductor properties are to be found in only a very limited number of materials. The materials used in general are certain perovskites which are generally doped with other cations to increase the conductivity properties and the thermal stability.

There are a number of publications describing such materials and mixed conducting membranes produced therewith.

U.S. Pat. No. 4,791,079 and U.S. Pat. No. 4,827,071 describe mixed conducting, oxide ion selective membranes that are comprised of zirconia doped with a metal of group VB, VIB or titanium dioxide. The preferred ceramic material used is zirconia doped with yttria and titania. The membrane supports a porous material containing an oxidation catalyst for hydrocarbons. Depending on the nature of this catalyst, the membranes thus obtained are useful in various oxidation reactions, for example the production of ethylene oxide or propylene oxide from the respective olefin, the oxidative dehydrogenation of monoolefins or the oxidative coupling of methane or other alkanes.

EP-A-663 232 describes a mixed conducting, oxide ion selective membrane comprised of a metal oxide comprising a plurality of different metal ions and of a catalyst applied thereto. The oxide preferably comprises bismuth, barium, vanadium, molybdenum, cerium, ruthenium, manganese, cobalt, rhodium or praseodymium ions. The catalyst is preferably formed of a metal selected from the group consisting of platinum, palladium, gold and silver. The membrane catalysts thus obtained are useful for various oxidations, for example the conversion of methane to syngas, but also the conversion of oxides of, for example, sulfur or nitrogen into the respective elements, for example the conversion of sulfur oxides into sulfur and oxygen.

WO98/41394 teaches an oxide ion selective membrane of the general formula $ABO_{3-\delta}$, where A is one or more of calcium, strontium, barium, yttrium and lanthanum, B is one or more of chromium, manganese, iron, cobalt, nickel and copper, and $\delta$ ranges from 0 to 0.5.

The membrane has a catalyst on both sides, namely a catalyst for activating oxygen on one side and a hydrocarbon partial oxidation catalyst on the other. A catalyst of such a composition is useful for example for selectively carrying out the partial oxidation of methane to carbon monoxide and hydrogen.

WO 99/21649 describes a reactor membrane comprised of a mixed conducting, oxide ion selective membrane coated with the oxidation catalyst. The membrane is an oxidic compound of a plurality of metals selected from the group consisting of lanthanides, yttrium, 3d transition metals and group 13 metals. A multiplicity of oxidation catalysts, both oxidic and metallic, that can be applied to such membranes are disclosed.

However, all the oxidation reactions mentioned in the above-cited references are generally carried out at high temperatures, generally about 800 to 1000° C. This is because prior art mixed conducting, oxide ion selective membranes need such high temperatures to provide an oxygen permeance sufficient for industrial application. Below the temperature range mentioned, the oxygen diffusion coefficient of the above-disclosed materials is so small that insufficient oxygen migrates through the membrane. The use of these mixed conducting membranes in oxidation reactions is thus generally restricted to oxidation reactions that proceed in the temperature range mentioned. It would be desirable, however, to have oxidation catalysts on mixed conducting, oxide ion selective membranes that can also be used at relatively low temperatures.

DISCLOSURE OF INVENTION

It is an object of the present invention to provide such a reactor membrane. It shall retain the previously known advantages of oxidation catalysts applied to mixed conducting membranes. This is in particular the elimination of the need for an air separation in those cases where the particular oxidation reaction has to be carried out with pure oxygen. In addition, the selectivity of the oxidation is frequently enhanced by making the oxygen available as lattice oxygen at the catalyst/reaction gas phase boundary. Unwanted secondary reactions taking place homogeneously in the gas phase are suppressed.

We have found that this object is achieved by a reactor membrane comprising a selective oxidation catalyst on a mixed conducting, oxide ion selective ceramic membrane of the composition $(Sr_{1-x}Ca_x)_{1-y}A_yMn_{1-z}B_zO_{3-\delta}$ where A is Ba, Pb, Na, K, Y, an element of the lanthanide group or a combination thereof, B is Mg, Al, G, In, Sn, an element of the 3d or 4d series or a combination thereof, x is from 0.2 to 0.8, y is from 0 to 0.4, z is from 0 to 0.6, and $\delta$ is a number, dependent on x, y or z, that renders the composition charge neutral.

This invention further provides for the use of the above-described reactor membrane in oxidation reactions of hydrocarbons using oxygen.

The reactor membrane of the invention or its use in oxidation reactions makes it possible to conduct these reactions at previously impossible temperatures. This temperature range extends in particular from 350 to 450° C. A decisive aspect of the reactor membrane according to the invention is the mixed conducting, oxide ion selective membrane.

Useful mixed conducting membranes include the mixed conducting membranes disclosed in German Application 198 26 496.8. They are oxides derived from β-SrMnO$_3$, an ABO$_3$-structured perovskite. This SrMnO$_3$ has added to it certain foreign ions to enhance the thermal stability and the oxide ion permeability.

These foreign ions include, first, a cation having a smaller ionic radius than strontium. If the base material is modified in this way, $Ca^{2+}$ is added in any case to obtain a compound having the composition $Sr_{1-x}Ca_xMnO_{3-\delta}$. If desired, a further ion smaller than strontium and identified above as A can be incorporated. This further ion A is selected from the group consisting of Ba, Pb, Na, K and Y. The resulting compounds have the general formula $(Sr_{1-x}Ca_x)_{1-y}A_yMnO_{3-\delta}$, where x, y and $\delta$ are each as defined above.

Furthermore, manganese can be replaced with a cation having a larger ionic radius, this cation being referred to as B hereinbelow. B can be an element of the $3^{rd}$ main group, preferably $Al^{3+}$, $Ga^{3+}$ or $In^{3+}$ or an element of the 3d or 4d series, for example $Fe^{3+}$, $Co^{2+}$ or $Ni^{2+}$. The particular advantage of incorporating a metal of valency <4 is the resulting higher conductivity for the material. Incorporation of cation B gives compounds of the general formula $SrMn_{1-z}B_zO_{3-\delta}$, where z and $\delta$ are each as defined above.

In a further modification, strontium and manganese can be replaced at one and the same time. This produces compounds of the general formula $(Sr_{1-x}Ca_x)_{1-y}A_yMn_{1-z}B_zO_{3-\delta}$, where x, y, z and $\delta$ are each as defined above.

One advantage of such mixed conducting membranes is that $O_2$ diffusion coefficients of about $10^{-7}$ cm$^2$/s are obtained at as low as about 220° C. This makes it technologically interesting to use such membranes as part of reactor membranes for selective catalytic oxidations. Prior art mixed conducting membranes have application temperatures >700° C., distinctly too high for such selective catalytic oxidations.

The membranes described may include other materials that conduct oxide ions or electrons. To preserve the advantageous properties of the membrane, however, it should account for more than 10% by volume of the ceramic material according to the invention. Furthermore, the membrane described can be applied to a porous support material whose pore fraction ranges from 10 to 85%.

That content of German Application 198 26 496.8 which refers to the mixed conducting membrane and its preparation forms an important and integral part of the present invention and is incorporated herein by reference.

Selective oxidation catalysts which, according to the invention, can be applied to the above-described membrane include selective oxidation catalysts that are used in the commonly known oxidation reactions of hydrocarbons. Examples of such oxidation reactions and the catalysts used will now be given.

Ammoxidation of Propane to Acrylonitrile

Catalysts used have the composition Mo—V—Te—X—O, for example, where X is Nb, Ta, W, Ti, Al, Zr, Cr, Mn, Fe, Ru, Co, Rh, Ni, Pd, Pt, Sb, Be, B, In, Ce. A description of the catalysts of this type is given in EP-A-603 836.

Ammoxidation of Propene to Acrylonitrile

Mo-, Bi- and Fe-containing catalysts can be used for example. These are described for example in EP-A-807 622.

Ammoxidation of o-m-p-xylene

V- and Sb-containing catalysts can be used for example. Such catalysts are described for example in EP-A-222 249.

Oxidation of n-butane, n-butene or Butadiene to Maleic Anhydride

Oxidic vanadium- and phosphorus-containing catalysts can be used, as described for example in EP-A-646 045.

Oxidation of o-xylene to Phthalic Anhydride

Oxidic vanadium- and titanium-containing catalysts are used for example, and they are described for example in DE-A-197 07 943.

Ammoxidation of o-xylene to Phthalonitrile

V- and Sb-containing catalysts can be used for example, as is described for example in EP-A-222 249.

Oxidation of Propene to Acrolein

Here, oxidic molybdenum-, bismuth- and iron-containing catalysts can be used, as is disclosed for example in EP-A-575 897.

Gas Phase Oxidation of Acrolein to Acrylic Acid

It is advantageous to use Mo- and V-containing catalysts, for example those disclosed in EP-A-17 000 or EP-A-774 297.

Oxidation of Methacrolein to Methacrylic Acid

Cesium-, molybdenum-, phosphorus- and vanadium-containing catalysts are used. This is described for example in EP-A-668 103.

Oxidative Dehydrogenations

In general, all known oxydehydrogenation catalysts can be used.

To dehydrogenate propane to propene, for example, oxidic molybdenum- and cobalt-containing catalysts are used. This is described for example in WO 99/42404.

Butenes can be dehydrogenated to butadiene using for example oxidic antimony- and iron-containing catalysts. This is disclosed for example in U.S. Pat. No. 3,445,521.

To dehydrogenate ethylbenzene to styrene all known oxydehydrogenation catalysts can be used.

The oxidative dehydrogenation of methanol to formaldehyde is carried out using oxidic iron- and molybdenum-containing catalysts, as is disclosed for example in DE-A-24 42 311, EP-A-423 692 or EP-A-591 572.

The membrane-mounted oxidation catalyst is most simply porous and/or has been applied to a porous material. In a preferred embodiment, the oxidation catalyst is a material which is itself mixed conducting and oxide ion selective. The advantage of such an embodiment is that in this case the catalyst can be applied to the actual mixed conducting membrane without through connected pores. As a result, the reaction gas can be protected if the membrane material has an undesirable catalytic effect on it.

The thickness of the catalyst layer is from 10 Å to 1 mm. The catalyst layer may for example have an asymmetrical construction such that the zone adjoining the mixed conducting layer is pore free. This zone is in turn adjoined by a zone that has an open porosity toward the reaction mixture.

In a preferred embodiment of the present invention, there is an oxidic interlayer from 10 Å to 10 $\mu$m in thickness between the mixed conducting membrane and the oxidation catalyst. This layer serves to enhance the mechanical strength and/or to facilitate the passage of the charged species from the membrane into the catalyst layer and vice versa.

The reactor membrane of the invention, comprising an oxidation catalyst, can have different configurations. In one embodiment the membrane is flat and the catalyst is applied to one side of the membrane. In another embodiment, the membrane has a tube geometry with diameters from 4 to 100 mm. Depending on the envisioned use, the catalyst layer is applied to the outer surface or to the inner surface. It will be appreciated that the form of the reactor membrane with the oxidation catalyst is not restricted to the geometries described above, but that the membrane can also be present in other geometries and forms known to one skilled in the art.

The oxidation catalyst is applied to the membrane using customary methods known to one skilled in the art. These methods include for example sol-gel deposition, sputtering, precipitation, crystallization, chemical vapor deposition, physical vapor deposition or slip coating. After this catalyst has been applied to the membrane, the product obtained is brought into the ready-to-use state by customary methods, for example by heat treatment, at high temperatures which lead to sintering, including in specific gas atmospheres, for example inert gas, oxygen or air.

The ready-produced reactor membrane according to the invention is then used in the particular oxidation reaction where an oxygen-containing fluid will contact the membrane on that side which is not coated with catalyst. The oxygen-containing fluid used is air or air with modified oxygen fraction, although in each case further components, which may be vaporizable, can be present. The pressure acting on this fluid is from 0.1 to 100 bar, preferably from 0.6 to 50 bar, most preferably from 0.6 to 30 bar.

That side of the membrane supporting the oxidation catalyst is then during the reaction the location for the mixture containing the component to be oxidized. This mixture can be gaseous, liquid or a mixture of gaseous and liquid components. This mixture is under the same pressures as the oxygen-containing fluid, namely from 0.1 to 100 bar, preferably from 0.6 to 50 bar, most preferably from 0.6 to 30 bar.

In one embodiment of the reactor membrane, the side facing the oxygen-containing fluid supports a redox catalyst that catalyzes the conversion of molecular oxygen into oxide ions and hence facilitates the entry of the oxygen into the membrane. Such redox catalysts are described for example in Solid State Ionics 113 to 115 (1998), p. 639 ff.

Owing to the considerable evolution of heat, the oxidation reaction is advantageously conducted in such a way that cooling is applied between a plurality of zones disposed along the direction of flow of the reaction gas. This cooling is effected in a customary manner known to one skilled in the art. For example, the reaction can be carried out in such a way that a fluid is introduced between a plurality of zones disposed along the direction of flow of the reaction mixture, the temperature of this fluid being below that of the reaction gas entering the zone. In many cases this provides an adequate cooling effect. Useful fluid media include for example water or water vapor, oxygen, air or air having a modified oxygen fraction, nitrogen or ammonia.

A cooling effect can also be provided by providing a boiling medium on one side of the membrane. Boiling will in many cases provide effective cooling to the membrane. It is also possible to cool by heat transfer between either or both streams leaving the reactor and the corresponding streams entering the reactor. Such an embodiment has the advantage that the excess heat evolved in the oxidation reaction can be used for heating the reactant mixture.

In a preferred embodiment of the present invention, the oxidation reaction takes place in a tubular reactor, in which case the reactor membrane of the invention has to have the appropriate shape, of course. Some of the tubes are used for cooling, according to the above-explained methods. Preferably, such cooling in a tubular reactor takes the form of evaporating a suitable medium.

The reactor membrane of the invention can be used in customary reactors made of materials known to one skilled in the art. Examples of such materials are carbon steel, stainless steel or Hastelloy. It is particularly advantageous for the membrane to be used in a reactor made entirely of ceramic materials. This eliminates any problems due to differences in the expansion coefficients of the reactor material and of the membrane material.

The inventive reactor membranes with the applied oxidation catalyst can be used with advantage in oxidations in the temperature range from 200 to 600° C., preferably from 300 to 500° C. This is not possible with prior art membranes. The reactor membranes according to the present invention, however, are also useful, it will be appreciated, in oxidations at temperatures higher than indicated, for example up to 1200° C. The reactor membranes of the invention can be used in all oxidation reactions that take place in the temperature range from 200 to 1200° C.

MODE(S) FOR CARRYING OUT THE INVENTION

The example hereinbelow illustrates the invention.

EXAMPLE

Oxidation of n-butane in an Oxidation Membrane Reactor

A porous magnesium oxide tube (average pore size 2 $\mu$m) 10 mm in external diameter, 7 mm in internal diameter and 20 cm in length was used as support. A finely divided powder of composition $Sr_{0.5}Ca_{0.5}MnO_{3-\delta}$ was made up into an aqueous slip. The inner surface of the aforementioned porous tube was dip coated. Thermal treatment at 1200° C. led to a porous layer 20 $\mu$m in thickness with an open porosity of 45% and an average pore size of 0.7 $\mu$m. This layer was dip coated with a thin layer of $Sr_{0.5}Ca_{0.5}MnO_{3-\delta}$ by the sol-gel technique. Thermal treatment led to a dense layer from 1 to 2 $\mu$m in thickness.

This layer on the inside of the tube was dip coated with a suspension of 235 g of $(VO)_2P_2O_7$ (prepared according to EP 39 537), particles having an average size of 5 $\mu$m, 800 ml of water and 100 ml of glycerol as adhesive to form a catalyst layer about 50 $\mu$m in thickness. The applied catalyst layer was dried and the adherent glycerol removed by heating the coated tube at 110° C. for 5 h and then at 250° C. for 10 h.

A stream of 10 standard 1/h of n-butane was directed through the tube. The outer surface of the tube was contacted with 50 standard 1/h of air. The two gas streams were preheated to 420° C. prior to entry into the reactor. The reactor membrane was likewise temperature controlled to 420° C.

The resulting reaction mixture was analyzed by gas chromatography. Maleic anhydride was found to have been formed at a rate of 0.1 mol of maleic anhydride per hour per m² of membrane surface.

We claim:

1. A reactor membrane comprising a selective oxidation catalyst on a mixed conducting, oxide ion selective ceramic membrane having a composition

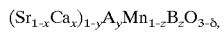

$(Sr_{1-x}Ca_x)_{1-y}A_yMn_{1-z}B_zO_{3-\delta}$, where

A is Ba, Pb, Na, K, Y, an element of the lanthanide group or combinations thereof, B is Mg, Al, Ga, In, Sn, an element of series 3d or 4d, or combinations thereof, x is from 0.2 to 0.8, y is from 0 to 0.4, z is from 0 to 0.6, and δ is a number, dependent on x, y and z, that renders the composition charge neutral.

2. A reactor membrane as claimed in claim 1, which is flat or has a tube geometry with an internal diameter from 4 to 100 mm.

3. A reactor membrane as claimed in claim 1, wherein the catalyst is a porous layer or itself has mixed conducting, oxide ion selective properties.

4. A reactor membrane as claimed in any of claims 1, wherein the catalyst has been applied to said membrane in a layer thickness from 10 Å to 1 mm.

5. A reactor membrane as claimed in any of claims 1, comprising an oxidic interlayer from 10 Å to 1 μm in thickness between said membrane and said oxidation catalyst.

6. A reactor membrane as claimed is claim 1, wherein the selective oxidation catalyst is a catalyst conventionally employed in a process for oxidizing hydrocarbons.

7. A process for oxidizing hydrocarbons comprising reacting the hydrocarbons and oxygen in the presence of the reactor membrane defined in claim 1.

8. A process of claim 7, wherein the oxidation reaction is carried out at a temperature of from 200 to 1200° C.

9. The process of claim 8, wherein the temperature is from 200 to 600° C.

10. The process of claim 8, wherein the temperature is from 300 to 500° C.

11. The process of claim 7, wherein the oxidation reaction is an ammoxidation, an oxidation of linear $C_4$ hydrocarbons to obtain maleic anhydride, an oxidation of o-xylene to obtain phthalic anhydride, a synthesis of (meth)acrolein or (meth)acrylic acid from corresponding hydrocarbons, an oxidative dehydrogenation of an alkane to obtain an alkene, or an oxidative dehydrogenation of an alcohol to obtain an aldehyde.

12. The process of claim 7, wherein oxygen is used in form of air or air having a modified oxygen fraction, optionally in the presence of a further vaporized fluid component.

13. The process of claim 7, wherein the oxidation catalyst is applied to one side of the reactor membrane.

14. The process of claim 13, which is conducted under pressure, the pressure on the side of said membrane to which said catalyst has been applied is from 0.1 to 100 bar, and the pressure on the side of said membrane on which said catalyst is not located is from 0.1 to 100 bar.

15. The process of claim 14, wherein the pressure on the side of said membrane which carries said catalyst is from 0.6 to 50 bar, and the pressure on the side of said membrane which does not carry said catalyst is from 0.6 to 50 bar.

16. The process of claim 14, wherein the pressure on the side of said membrane which carries said catalyst is from 0.6 to 30 bar, and the pressure on the side of said membrane which does not carry said catalyst is from 0.6 to 30 bar.

* * * * *

UNITED STATES PATENT AND TRADEMARK OFFICE
CERTIFICATE OF CORRECTION

PATENT NO. : 6,730,808 B2
DATED : May 4, 2004
INVENTOR(S) : Bitterlich et al.

It is certified that error appears in the above-identified patent and that said Letters Patent is hereby corrected as shown below:

Title page,
Item [75], Inventors, "Voigt" should be -- Voight --.

Column 7,
Lines 36 and 38, delete "any of claims" and insert -- claim --.

Signed and Sealed this

Eleventh Day of January, 2005

JON W. DUDAS
*Director of the United States Patent and Trademark Office*